UNITED STATES PATENT

US011491109B2

(12) United States Patent
Alsenz et al.

(10) Patent No.: US 11,491,109 B2
(45) Date of Patent: Nov. 8, 2022

(54) PHARMACEUTICAL COMPOSITIONS FOR BASIC OR NEUTRAL, LOW MOLECULAR WEIGHT COMPOUNDS

(71) Applicant: Hoffmann-La Roche Inc., Little Falls, NJ (US)

(72) Inventors: Jochem Alsenz, Basel (CH); Martin Kuentz, Muttenz (CH); Alfred Ross, Basel (CH); Wiebke Svea Saal, Basel (CH); Nicole Wyttenbach, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/791,230

(22) Filed: Feb. 14, 2020

(65) Prior Publication Data

US 2020/0206133 A1 Jul. 2, 2020

Related U.S. Application Data

(63) Continuation of application No. PCT/EP2018/072159, filed on Aug. 16, 2018.

(30) Foreign Application Priority Data

Aug. 17, 2017 (EP) ..................... 17186559

(51) Int. Cl.
*A61K 9/08* (2006.01)
*A61K 47/59* (2017.01)
*A61K 9/00* (2006.01)

(52) U.S. Cl.
CPC .............. *A61K 9/08* (2013.01); *A61K 47/593* (2017.08); *A61K 9/0014* (2013.01); *A61K 9/0053* (2013.01)

(58) Field of Classification Search
CPC ................................ A61K 47/32; A61L 31/16
See application file for complete search history.

(56) References Cited

U.S. PATENT DOCUMENTS

| 2006/0039981 A1* | 2/2006 | Murpani ................ A61K 47/32 424/487 |
| 2008/0095838 A1 | 4/2008 | Abou Chacra-Vernet |
| 2009/0074872 A1* | 3/2009 | Arnold ................. A61K 9/0095 424/489 |

FOREIGN PATENT DOCUMENTS

| JP | 2005-533802 | 11/2005 | |
| JP | 2006-502156 | 1/2006 | |
| JP | 2009-541485 | 11/2009 | |
| WO | 2004/022037 | 3/2004 | |
| WO | 2004/096182 A1 | 11/2004 | |
| WO | WO-2004096182 A1 * | 11/2004 | ................ A61P 9/10 |
| WO | 2008/002568 | 1/2008 | |

OTHER PUBLICATIONS

Kesharwani et al (Frontiers, Molecular complexation of curcumin with Eudragit® EPO to enhance the aqueous solubility, stability and bioavailability of curcumin, Abstract from 10th World Biomaterials Congress in Montreal, Canada, Published Mar. 30, 2016 online) (Year: 2016).*
Kumar et al (European Journal of Pharmaceutical Sciences, online Nov. 2015, vol. 82, pp. 86-96) (Year: 2015).*
Clinicalgate.com (Solutions, Aug. 2, 2015, https://clinicalgate.com/solutions/) (Year: 2015).*
Bergstrom, C., et al., "Experimental and Computational Screening Models for Prediction of Aqueous Drug Solubility" Pharm Res 19(2):182-188 (Feb. 1, 2002).
Desai, P., et al., "Overcoming poor oral bioavailability using nanoparticle formulations—opportunities and limitations" Drug Discov Today 9(2):e87-e95 (Summer 2012).
Dobrynin, A., et al., "Theory of polyelectrolytes in solutions and at surfaces" Prog Polymer Sci 30(11):1049-1118 (Nov. 1, 2005).
Doreth, M., et al., "Glass solution formation in water—In situ amorphization of naproxen and ibuprofen with Eudragit® EPO" J Drug Deliv Sci Tech 34:32-40 (Aug. 1, 2016).
Gallardo, D., et al., "Controlled Release Solid Dosage Forms Using Combinations of (meth)acrylate Copolymers" Pharm Dev Technol 13(5):413-423 (Oct. 20, 2008).
Higashi, K., et al., "Insights into Atomic-Level Interaction between Mefenamic Acid and Eudragit EPO in a Supersaturated Solution by High-Resolution Magic-Angle Spinning NMR Spectroscopy" Mol Pharmaceutics 11(1):351-357 (Nov. 27, 2013).
Higashi, K., et al., "Mechanistic insight into the dramatic improvement of probucol dissolution in neutral solutions by solid dispersion in Eudragit E PO with saccharin" J Pharm Pharmacol 68(5):655-664 (May 1, 2016).
Humberstone, A., et al., "Lipid-based vehicles for the oral delivery of poorly water soluble drugs" Adv Drug Deliver Rev 25(1):103-128 (Apr. 14, 1997).
"International Preliminary Report on Patentability—PCT/EP2018/072159":pp. 1-8 (dated Feb. 27, 2020).
"International Search Report—PCT/EP2018/072159":pp. 1-5 (dated Oct. 19, 2018).
Kanaya, H., et al., "Stabilization mechanism of nitrazepam supersaturated state in nitrazepam/Eudragit® EPO/saccharin solution revealed by NMR measurements" Asian J Pharm Sci 11(1):58-59 (Nov. 23, 2015).
Kirchmeyer, W., et al., "Influence of Excipients on Solvent-Mediated Hydrate Formation of Piroxicam Studied by Dynamic Imaging and Fractal Analysis" Cryst Growth Des 15(10):5002-5010 (Sep. 14, 2015).
Kojima, T., et al., "Stabilization of a Supersaturated Solution of Mefenamic Acid from a Solid Dispersion with Eudragit® EPO" Pharm Res 29:2777-2791 (Jan. 5, 2012).
Kuentz, Martin, "Lipid-based formulations for oral delivery of lipophilic drugs" Drug Discov Today 9(2):e97-e104 (Summer 2012).

(Continued)

*Primary Examiner* — Mark V Stevens
(74) *Attorney, Agent, or Firm* — Katherine J. Mackenzie

(57) ABSTRACT

The present invention provides novel, solid or liquid pharmaceutical preparations comprising a basic or neutral, low molecular weight active pharmaceutical ingredient and the polymer Eudragit® EPO, optionally together with additional pharmaceutically acceptable excipients. The present preparations are for oral or topical administration.

10 Claims, 8 Drawing Sheets

(56) References Cited

OTHER PUBLICATIONS

Lee, Y., et al., "An intravenous formulation decision tree for discovery compound formulation development" Int J Pharm 253(1-2):111-119 (Mar. 6, 2003).
Li, J., et al., "Curcumin-Eudragit® E PO solid dispersion: A simple and potent method to solve the problems of curcumin" Eur J Pharm Biopharm 94:322-332 (Aug. 1, 2015).
Li, P., et al., "Developing early formulations: Practice and perspective" Int J Pharm 341(1-2):1-19 (Aug. 16, 2007).
Lipinski, C., et al., "Experimental and computational approaches to estimate solubility and permeability in drug discovery and development settings" Adv Drug Deliver Rev 23(1-3):3-26 (Jan. 15, 1997).
Priemel, P., et al., "In situ amorphisation of indomethacin with Eudragit® E during dissolution" Eur J Pharm Biopharm 85(3 Suppl Part B):1259-1265 (Nov. 1, 2013).
Saal, W., et al., "A Systematic Study of Molecular Interactions of Anionic Drugs with a Dimethylaminoethyl Methacrylate Copolymer Regarding Solubility Enhancement" Mol Pharmaceutics 14(4):1243-1250 (Mar. 13, 2017).
Serajuddin, Abu, "Solid dispersion of poorly water-soluble drugs: Early promises, subsequent problems, and recent breakthroughs" J Pharm Sci 88(10):1058-1066 (Oct. 1, 1999).
Solis, F., et al., "Collapse of flexible polyelectrolytes in multivalent salt solutions" J Chem Phys 112(4):2030-2035 (Jan. 22, 2000).
Song, Y., et al., "Investigation of Drug—Excipient Interactions in Lapatinib Amorphous Solid Dispersions Using Solid-State NMR Spectroscopy" Mol Pharmaceutics 12(3):857-866 (Jan. 13, 2015).
Van den Mooter, Guy, "The use of amorphous solid dispersions: a formulation strategy to overcome poor solubility and dissolution rate" Drug Discov Today 9(2):e79-e85 (Summer 2012).
Vö lgyi, G. et al., "Study of pH-dependent solubility of organic bases. Revisit of Henderson-Hasselbalch relationship" Anal Chim Acta 673(11):40-46 (Jul. 12, 2010).
Yalkowsky, S., et al. Handbook of Aqueous Solubility Data Second edition, Boca Raton, FL—US:CRC Press—Taylor & Francis Group,:1-1620 (Apr. 19, 2016).

\* cited by examiner

PHARMACEUTICAL COMPOSITIONS FOR BASIC OR NEUTRAL, LOW MOLECULAR WEIGHT COMPOUNDS

CROSS REFERENCE TO RELATED APPLICATIONS

This application is a continuation of International Application No. PCT/EP2018/072159, filed Aug. 16, 2018, which claims benefit of priority to EP Application No. 17186559.5 filed Aug. 17, 2017, each of which is incorporated herein by reference in its entirety.

FIELD OF THE INVENTION

The present invention related to the field of solid or liquid, preferably aqueous, pharmaceutical compositions for the administration of low molecular weight basic or neutral active pharmaceutically ingredients (API).

BACKGROUND OF THE INVENTION

Poorly water soluble drug candidates are becoming more prevalent in pharmaceutical discovery and development.[1, 2] These candidates can be formulated for oral administration by several strategies including the reduction of the particle size, formulation of the drug in solution, amorphous systems or lipid formulations.[3-6] While such formulation techniques are used in preclinical formulation supply, there are limitations of any sophisticated formulation approaches because of limited compound availability and stretched timelines.[7] Formulation strategies that are widely used in the early phase are solubilization by pH-adjustment, the use of cosolvents, cyclodextrins or surfactants, formulation as suspensions, emulsions, or solid dispersions.[7] Reports indicate that a great portion of compounds submitted for discovery and pre-clinical formulation development were formulated by pH adjustment, cosolvent addition, or a combination of the two approaches.[8] More complicated and metastable formulations such as solid dispersions are often not the first choice at an early development stage, for example, in preclinical formulation supply. However, much can be learned from the literature on solid dispersions regarding drug-polymer interactions that can be harnessed more broadly in different formulation approaches.[9-11] Eudragit® EPO (EPO) is known in the art as pharmaceutical polymer for taste masking, moisture protection, and enteric film-coating.[12] but more recently, it was used for solubility enhancement of poorly soluble acidic drugs by stabilizing them in an amorphous state.[13-17]

When using EPO as a carrier for amorphous compounds, outstanding results were obtained in terms of solubility and bioavailability enhancement.[14, 15] EPO was not only useful in stabilizing compounds in an amorphous state but improved solubilization was also demonstrated with a range of acidic drugs.[18] Only very few non-acidic compounds have so far been formulated with EPO[19, 20] and no data are available using only EPO for solubility enhancement of basic and neutral APIs. Therefore, there remains a need for further solid or liquid, preferably aqueous, pharmaceutical preparations comprising a lipophilic low molecular weight, basic or neutral, preferably basic API. The present invention provides such preparations. Based on studies with a series of model compounds, it has surprisingly been found that stable aqueous solution preparations of basic or neutral, low molecular API can be obtained when adding EPO as sole excipient.

DETAILED DESCRIPTION OF THE INVENTION

Figure 1:
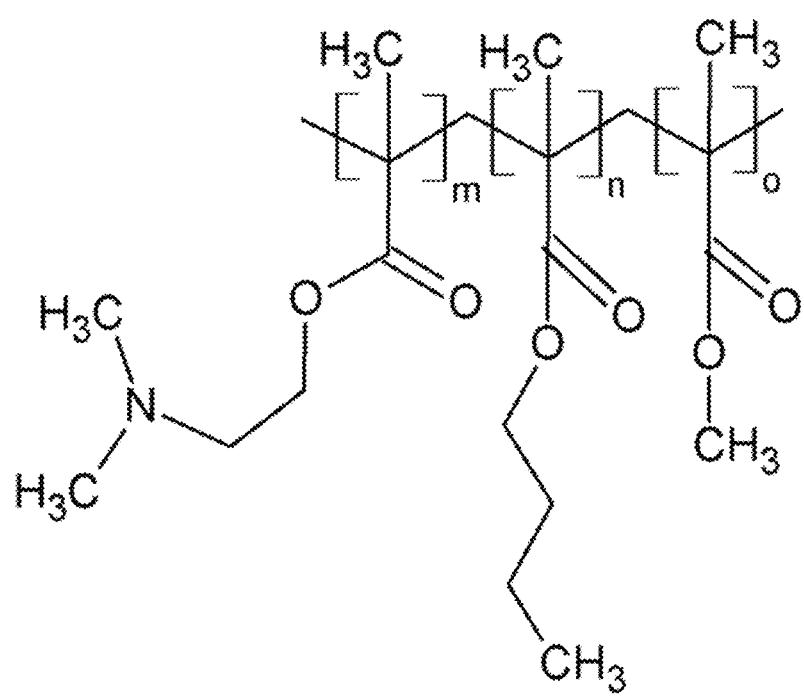
FIG. 1: Molecular structure of EPO

According to the present invention, there are disclosed methods for solubilization of lipophilic, basic or neutral, APIs by EPO. The findings in accordance with the present invention are surprising because in particular the bases and EPO exhibit positive charges at pH values <8. The present inventors obtained concentration dependent solubility data which demonstrate that EPO has a beneficial effect on drug solubility of the basic and neutral model drugs. Therefore, in accordance with the present invention, an unexpected and surprising increase in solubilization of said basic or neutral, but especially basic API's was demonstrated. In particular half of the tested basic drugs showed a plateau regarding solubility enhancement starting at 2% EPO.

The present inventors investigated the API-polymer-interactions in detail by means of solution NMR spectroscopy. The NMR spectra of the APIs together with EPO display a change in peak width for the aromatic region indicating their interaction with the polymer. The diffusion coefficients of the basic APIs decrease slightly in presence of the polymer (Table 6). The decrease in diffusion coefficient suggests that some percentage of the active compound is associated with the polymer. Such binding could be readily quantified if the polymer itself keeps its value of the diffusion coefficient in presence of drug. However, this is interestingly not the case and EPO appears to undergo itself diffusional changes because of the APIs (Table 6). Such a clear effect of altered EPO diffusion was not evidenced in a previous study of tested acidic compounds.[18] According to the present invention, the diffusion coefficient of the macromolecule (EPO) indicates that it is diffusing faster in the presence of basic drugs compared to pure water. Faster movement of the polymer must be associated with conformational changes of the macromolecule in solution. Accordingly, but without being bound to theory, complex drug-excipient interactions as evidenced by the present NMR results may form the basis of the surprisingly high drug solubilization enhancement in EPO solutions.

Eudragit® EPO (EPO) is positively charged at pH <8 and was earlier shown to be a solubilizer for negatively charged acidic drugs in different formulation approaches. According to the present invention the solubility of positively charged (basic) compounds can surprisingly also be enhanced by the addition of EPO to an aqueous solution comprising said compounds. The high extent of solubility enhancement is surprising given the same positive charge type of aminoalkyl groups that abundantly exist in EPO. The present invention thus broadens the application area of EPO, especially for simple formulations like suspensions and solutions that can be used in early phases of the drug development process.

Therefore, in one embodiment, the present invention provides a pharmaceutical preparation comprising a lipophilic, basic or neutral, low molecular weight active pharmaceutical ingredient and EPO, optionally together with additional pharmaceutically acceptable excipients The term "pharmaceutical preparation" comprises solid and liquid preparations which are both suitable for either oral or topic administration. In one embodiment the liquid pharmaceutical preparations is an aqueous preparation, preferably an aqueous preparation at physiological conditions.

The "additional pharmaceutically acceptable excipients" may vary according to either a solid or liquid pharmaceutical preparation (intermediate or final product) in accordance with the present invention. "Liquid pharmaceutical preparations" as used herein are prepared by mixing said lipophilic, basic or neutral, low molecular weight active pharmaceutical ingredient, having the desired degree of purity, with one or more optional "pharmaceutically acceptable carriers" in the form of aqueous solutions. "Pharmaceutically acceptable carriers", as used in combination with "liquid pharmaceutical preparations", are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyethylene glycol (PEG) or polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; further polyols such as sucrose, mannitol, trehalose or sorbitol; salt-forming counter-ions such as sodium; metal complexes (e.g. Zn-protein complexes); and/or ionic and non-ionic surfactants such as sodium dodecyl sulfate or poloxamers, respectively.

"Solid pharmaceutical preparations" (intermediate or final product) obtainable according to the present invention, can be used in a wide variety of forms for administration of said basic or neutral, low molecular weight active pharmaceutical ingredient, and in particular for oral or topic dosage forms. Exemplary dosage forms include powders or granules that can be taken orally either dry or reconstituted by addition of water to form a paste, slurry, suspension or solution; tablets, capsules, or pills. Various additives can be mixed, ground or granulated with the dispersion (molecularly or particulate dispersed) as described herein to form a material suitable for the above dosage forms. Potentially beneficial additives may fall generally into the following classes: other matrix materials or diluents, surface active agents, drug complexing agents or solubilizers, fillers, disintegrants, binders, lubricants, and pH modifiers (e.g., acids, bases, or buffers). Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. In addition to the above additives or excipients, use of any conventional materials and procedures for formulation and preparation of oral or topical dosage forms using the compositions disclosed herein known by those skilled in the art are potentially useful.

In one embodiment in accordance with the present invention the active pharmaceutical ingredient is basic.

In another embodiment in accordance with the present invention the active pharmaceutical ingredient is neutral.

The term "physiological conditions" means a pH value from about 1 to 8, preferably 4.0 to 7.0, more preferably from 5.5. to 6.5.

The term "EPO" or "Eudragit EPO", as used herein means a methacrylic acid copolymer composed of dimethylaminoethyl methacrylate, butyl methacrylate, and methyl methacrylate which is positively charged at pH <8 in aqueous media. In a preferred embodiment "EPO" or "Eudragit® EPO", as used herein means a methacrylic acid copolymer composed of dimethylaminoethyl methacrylate, butyl methacrylate, and methyl methacrylate with a molar ratio of 2:1:1. The chemical structure of EPO is displayed in FIG. 1.

In one embodiment according to the present invention, the term "basic, low molecular weight active pharmaceutical ingredient (API)" means any low molecular weight compound, or small molecule, which is positively charged and has pharmacological activity. In another embodiment, the term "basic" means that the compound has a pKa-value from about 5 to 14.

In one embodiment according to the present invention, the term "neutral, low molecular weight active pharmaceutical ingredient (API)" means any low molecular weight compound, or small molecule, which is not charged and has pharmacological activity. In another embodiment, the term "neutral" means that the compound has no ionizable group and/or a basic pKa-value <5.

The term "low molecular weight compound" or "small molecule" in connection with the neutral or basic compounds as defined herein means a compound having a molecular weight from about 100 g/mol to about 3000 g/mol, preferably 100 g/mol to about 1500 g/mol, more preferably 100 g/mol to about 1000 g/mol.

The term "lipophilic" as used herein means log P values >1.

The term "Active Pharmaceutical Ingredient (API)" means the compound or component of any drug that produces its effects.

In another embodiment the liquid pharmaceutical composition in accordance with the present invention comprises only water, the lipophilic, basic or neutral, low molecular weight active pharmaceutical ingredient and EPO.

In yet another embodiment, the liquid, preferably aqueous, pharmaceutical composition in accordance with the present invention comprises the lipophilic, basic low molecular weight active pharmaceutical ingredient in an amount from 0.000001% (w/w) to 20% (w/w), preferably 0.00001% (w/w) to 10% (w/w) and EPO in an amount from 0.01% (w/w) to 20% (w/w), preferably 0.1%, 0.5%, 1%, 2%, 3%, 4% or 5% (w/w).

In yet another embodiment, the liquid, preferably aqueous, pharmaceutical composition in accordance with the present invention comprises the lipophilic, neutral low molecular weight active pharmaceutical ingredient in an amount from 0.000001% (w/w) to 20% (w/w), preferably 0.00001% (w/w) to 10% (w/w) and EPO in an amount from 0.01% (w/w) to 20% (w/w), preferably 0.1%, 0.5%, 1%, 2%, 3%, 4% or 5% (w/w).

The term "weight %" as used herein is sometimes also designated as "% (w/w)".

In yet another embodiment, the present invention provides the pharmaceutical preparation as defined herein for use as a medicament.

In yet another embodiment, the present invention provides the pharmaceutical preparation as defined herein for oral use.

In yet another embodiment, the present invention provides vials containing the pharmaceutical preparation as defined herein.

In yet another embodiment, the present invention provides a kit comprising vials containing the pharmaceutical preparation as defined herein together with means for application to a patient in need of such administration, and further comprising instructions how to prepare and use said administration.

In yet another embodiment, the present invention provides a method of treating a patient, comprising administering to said patient the pharmaceutical preparation in accordance with the present invention.

Figure 2:
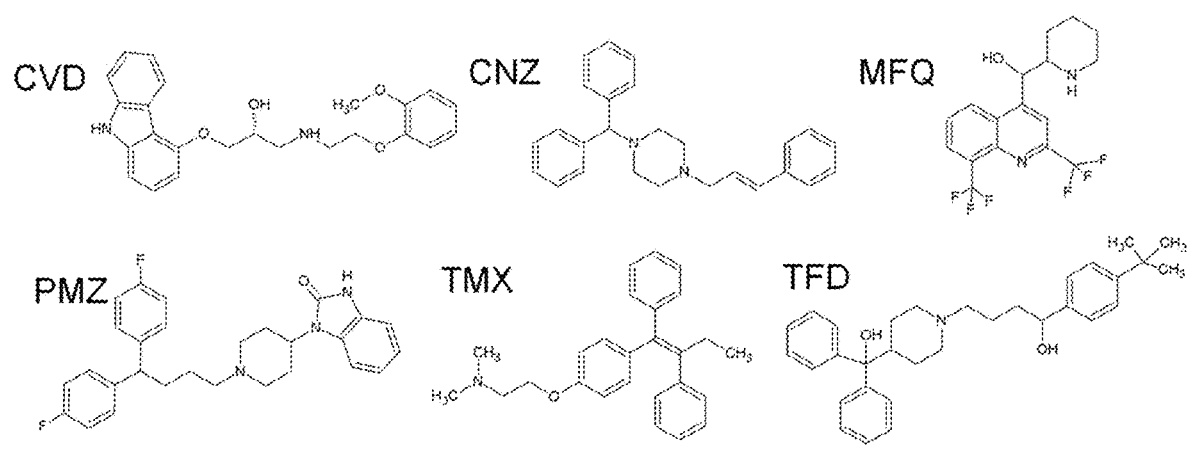
FIG. 2: Chemical structure of model drug bases and abbreviations used (from left to right in the order of carvedilol, cinnarizine, mefloquine, pimozide, tamoxifen, and terfenadine).

The invention will now be illustrated by the accompanying working examples, which are in no way meant to limit the scope of the claims. In the Examples, the following basic, low molecular weight model compounds were used:

Pimozide (PMZ) and tamoxifen (TMX) were obtained by Sigma Aldrich (Buchs, Switzerland), while carvedilol (CVD) was from AK Scientific, Inc. (Union City, USA). Cinnarizine (CNZ) was purchased from Alfa Aesar (Karlsruhe, Germany), mefloquine (MFQ) was obtained from F. Hoffmann-La Roche Ltd (Basel, Switzerland) and terfenadine (TFD) was from Carbosynth Ltd (Compton, UK). The chemical structures of all model compounds are shown in FIG. 2 and their physicochemical properties are listed in Table 1. Aminoalkyl metacrylate copolymer E, Eudragit® EPO, (EPO) was obtained by Evonik (Darmstadt, Germany). Hydrochloric acid (0.1 M) and sodium hydroxide solution (0.1 M) were from Merck KGaA (Darmstadt, Germany).

TABLE 1

Molecular weight (Mw), ionization constant (pKa) and distribution coefficient (logD) at pH 6.0 for the different model compounds.

| Compound | Mw [g/mol] | $pK_a{}^a$ | $LogD^b$ (pH 6.0) | $LogP^b$ |
|---|---|---|---|---|
| Carvedilol (CVD) | 406.5 | 8.1 | 0.8 | 3.4 |
| Cinnarizine (CNZ) | 368.5 | 7.8 | 3.8 | 5.9 |
| Mefloquine (MFQ) | 378.1 | 9.2 | 1.1 | 4.1 |
| Pimozide (PMZ) | 461.2 | 8.6 | 3.5 | 5.8 |
| Tamoxifen (TMX) | 371.2 | 9.7 | 3.7 | 6.4 |
| Terfenadine (TFD) | 471.7 | 9.1 | 3.6 | 6.5 |

$^a$Measured $pK_a$-values via photometric titration (Roche internal data)
$^b$Values calculated by Marvin Suite (V. 16.5.30, ChemAxon, Douglas Drake, USA)

Figure 7:
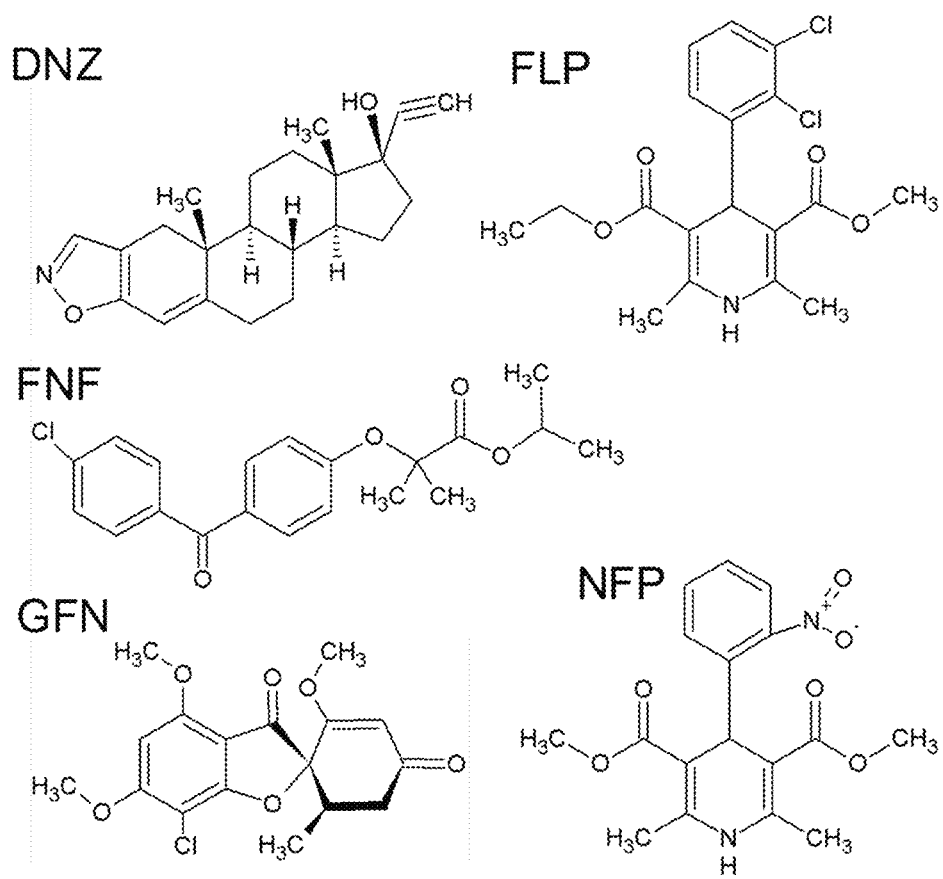
FIG. 7: Chemical structure of neutral model drugs and abbreviations used (from left to right in the order of danazol, felodipine, fenofibrate, griseofulvin and nifedipine).

In the Examples, the following neutral, low molecular weight model compounds were used: Danazol (DNZ), fenofibrate (FNF), griseofulvin (GFN), and nifedipine (NFP) were obtained by Sigma Aldrich (Buchs, Switzerland) while felodipine (FLP) was from Melrob-Eurolabs (Congleton, UK). The chemical structures of all neutral model compounds are shown in FIG. 7 and their physicochemical properties and aqueous solubility are listed in Table 1a. Aminoalkyl metacrylate copolymer E, Eudragit® EPO, (EPO) was obtained by Evonik (Darmstadt, Germany). Hydrochloric acid (0.1 M) and sodium hydroxide solution (0.1 M) were from Merck KGaA (Darmstadt, Germany).

TABLE 1a

Molecular weight (Mw), distribution coefficient (logD) at pH 6.0, and aqueous solubility for the different model compounds.

| Compound | Mw [g/mol] | $LogD^a$ (pH 6.0) | $LogP^a$ | Aqueous solubility (standard deviation, n = 3) [mg/ml] |
|---|---|---|---|---|
| Danazol (DNZ) | 337.5 | 3.5 | 3.5 | 0.002 (0.000) |
| Felodipine (FLP) | 384.3 | 3.4 | 3.4 | 0.0004 (0.0001) |
| Fenofibrate (FNF) | 360.8 | 5.3 | 5.3 | 0.0003* |
| Griseofulvin (GFN) | 352.8 | 2.2 | 2.2 | 0.012 (0.001) |
| Nifedipine (NFP) | 346.3 | 1.8 | 1.8 | 0.018 (0.001) |

$^a$Values calculated by Marvin Suite (V. 16.5.30, ChemAxon, Douglas Drake, USA).
*Solubility values below limit of detection, aqueous solubility from literature.[28]

EXAMPLES

Example 1

Sample Preparation

Polymer solutions were prepared by dissolving EPO (0.1%, 0.5%, 1%, 2%, 3%, 4%, 5% (w/w)) in deionized water and adjusting all solutions to pH 6.0 by hydrochloric acid and sodium hydroxide at 25° C. Solutions were checked carefully for absence of particles.

Solubility and Residual Solid Analysis

Solubility of compounds in EPO-solutions was determined by using a 96-well assay that was introduced to measure equilibrium solubility in parallel to a solid state analysis of the residual solid (SORESOS)[21] as described before.[22] In brief, APIs were dispensed using the powder-picking-method[23] in a 96-well flat bottom plate (Corning Inc., Durham, USA). Mixtures were agitated by head-over-head rotation for 48 h at room temperature after addition of stir bars and polymer solutions (150 μl). After mixing, the suspensions were carefully transferred into 96-well filter plates and the liquid and solid phase were separated by centrifugation. Filtrates were collected, diluted with N-methyl-2-pyrrolidone and drug content in filtrates was determined using a Waters Acquity Ultra Performance Liquid Chromatographic (UPLC) system equipped with a 2996 Photodiode Array Detector and an Acquity UPLC BEH C18 column (2.1×50 mm, 1.7 μm particle size) from Waters (Milford, USA). An isocratic flow (composition of the mobile phase is listed in Table 2) was applied for 0.3 min at a flow rate of 0.75 mL/min. Subsequently, the concentration of solvent B was linearly increased to 100% within 0.5 min. Solid state analysis of residual solid was performed by X-ray powder diffraction (XRPD) using a STOE Stadi P Combi diffractometer with a primary Ge-monochromator (Cu Kα radiation), imaging plate position sensitive detector (IP-PSD), and a 96-well sample stage as described before.[21] The IP-PSD allowed simultaneous recording of the diffraction pattern on both sides of the primary beam which were summed up by the software STOE WinXPOW to reduce effects related to poor crystal orientation statistics. Samples were analyzed directly in the 96-well filter plate with an exposure time of 5 min per well.

TABLE 2

UPLC analytic.

| | Gradient (A:B)[a] [%] | Detection wavelength [nm] |
|---|---|---|
| CVD | 80:20 | 331 |
| CNZ | 90:10 | 230 |
| MFQ | 90:10 | 222 |
| PMZ | 90:10 | 214 |
| TMX | 90:10 | 223 |
| TFD | 70:30 | 260 |

[a]Mobile phase A: deionized water with 0.1% (v/v) triethylamine adjusted to pH 2.2 with methanesulfonic acid
Mobile phase B: acetonitrile 1H-NMR Spectroscopy Solutions for NMR analyses were prepared by suspending APIs for 24 h in a 0.5% (w/w) EPO-solution in deuterium oxide ($D_2O$) at pH 6.0. Samples were then centrifuged and supernatants (550 µl) were transferred to short disposable 5 mm NMR tubes. All NMR measurements were performed with a Bruker 600 MHz Avance II spectrometer equipped with a cryogenic QCI probe head at a temperature of 300 K. Spectrometer operation and data processing was done by Topsin 2.1 software (Bruker, Fällanden, Switzerland). For all samples matching/tuning of the probe head and the 90° pulse were determined fully automated. Pseudo 2D $^1H$ diffusion ordered spectroscopy (DOSY) with bipolar gradient pulsepairs and 2 spoil gradients[24] was measured for all samples with resaturation of residual water. Data points (32 k) were acquired over 18 ppm sweep-width and the interscan delay was set to 1.5 s. SMSQ10.100 shaped bipolar gradient was ramped from 2.65 to 50.35 gauss/cm in 16 equidistant steps. Spectra were processed with a lb=1 exponential filtering
and a diffusion time of 300 ms was used. Diffusion coefficient D was fitted by use of the $T_1/T_2$ relaxation module implemented within the Topsin 2.1 software (Bruker, Switzerland). For most molecules at least one API and excipient related NMR signal was identified by visual inspection.

Results

Solubility and Residual Solid Analysis

Figure 3:
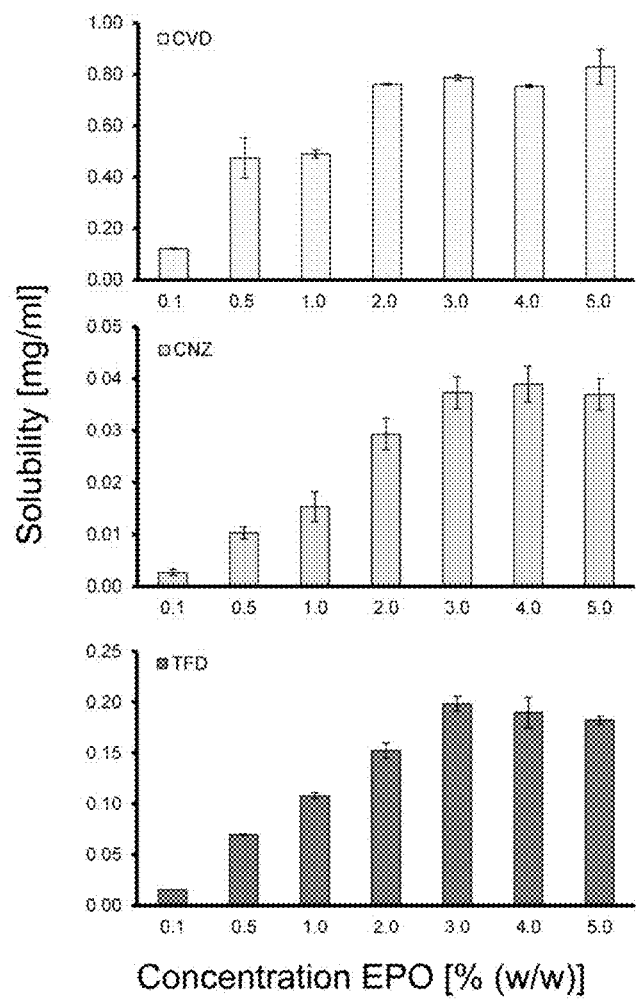
FIG. 3: Solubility of CVD, CNZ, and TFD in EPO-solutions after 48 h at room temperature.
Figure 4:
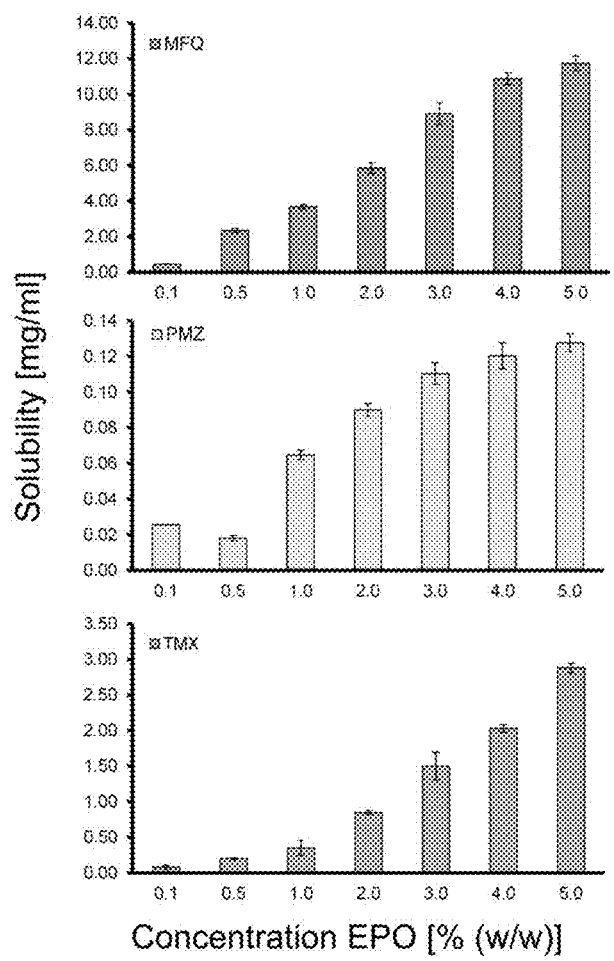
FIG. 4: Solubility of MFQ, PMZ, and TMX in EPO-solutions after 48 h at room temperature.

All excipient solutions were adjusted to pH 6.0 before incubation and following equilibration, the residual solid was analyzed by means of XRPD. Compared to water, all model compounds displayed a good solubility enhancement (SE) in the different EPO-solutions (FIGS. 3-4 and Table 5). In addition to the measured aqueous solubilities of the model compounds, adjusted solubility values for pH 6.0 are displayed in Table 3. This extrapolation method was based on the Henderson-Hasselbalch equation and it is generally reliable when the experimental solubility value is within one pH unit difference.[25]

TABLE 3

Drug solubility and pH of drug suspensions in water after 24 h incubation time. Aqueous solubilities were adjusted for a pH 6.0.

| Compound | Solubility in water (standard deviation, n = 3) [mg/ml] | pH in water (standard deviation, n = 3) | Adjusted solubility at pH 6.0 [mg/ml] |
|---|---|---|---|
| CVD | 0.005 (0.002) | 7.2 (0.3) | 0.071 |
| CNZ | 0.001 (0.001) | 6.1 (0.3) | 0.001 |
| MFQ | 0.063 (0.001) | 7.6 (0.1) | 2.448 |
| PMZ | 0.002 (0.001) | 6.8 (0.2) | 0.013 |
| TMX | 0.008 (0.004) | 6.9 (0.0) | 0.064 |
| TFD | 0.002 (0.001) | 6.8 (0.2) | 0.013 |

TABLE 4 pH of drug suspensions in the presence of 2% and 5% EPO after 48 h at room temperature.

| Compound | pH in EPO 0.5% after 48 h (Standard deviation, n = 3) | pH in EPO 2% after 48 h (Standard deviation, n = 3) | pH in EPO 5% after 48 h (Standard deviation, n = 3) |
|---|---|---|---|
| CVD | 5.9 (0.0) | 5.8 (0.1) | 6.0 (0.0) |
| CNZ | 5.7 (0.1) | 6.0 (0.0) | 5.9 (0.0) |
| MFQ | 6.3 (0.1) | 6.3 (0.0) | 6.4 (0.0) |
| PMZ | 5.8 (0.1) | 6.0 (0.0) | 6.0 (0.0) |
| TMX | 5.9 (0.1) | 5.9 (0.0) | 6.0 (0.0) |
| TFD | 5.8 (0.0) | 6.1 (0.0) | 6.0 (0.0) | pH values were also measured after 48 h for all basic compounds in EPO (0.5%, 2%, and 5%) and are shown in Table 4. The pH did not change for most compounds, only MFQ caused a pH increase to values of 6.3 and 6.4. Such a pH shift was expected given the dissolution of a basic compound. MFQ reached with 12 mg/ml at an EPO concentration of 5% the highest total solubility, which thereby caused the pH shift. CVD, CNZ, and TFD (FIG. 3) solubility reached a plateau at 2% EPO (w/w). In contrast, MFQ, PMZ, and TMX (FIG. 4) showed an increase of solubility with polymer concentration up to 5% EPO.

TABLE 5

Adjusted solubility enhancement (SE) factors of model compounds in EPO-solutions (0.1-5%) compared to solubility in water (pH 6.0). SE factors were calculated by dividing the solubility of a compound in polymer solutions by the adjusted solubility in water at a pH 6.0. Non-adjusted values are displayed in brackets.

| Compound | SE in EPO 0.1% | SE in EPO 0.5% | SE in EPO 1.0% | SE in EPO 2.0% | SE in EPO 3.0% | SE in EPO 4.0% | SE in EPO 5.0% |
|---|---|---|---|---|---|---|---|
| CVD | 1.7 (24.3) | 6.7 (94.9) | 6.9 (97.9) | 10.7 (152.3) | 11.1 (157.4) | 10.6 (150.9) | 11.7 (165.9) |
| CNZ | 2.7 (2.7) | 10.3 (10.3) | 15.3 (15.3) | 29.3 (29.3) | 37.3 (37.3) | 39.0 (39.0) | 37.0 (37.0) |
| MFQ | 0.2 (7.2) | 1.0 (37.3) | 1.5 (58.3) | 2.4 (92.8) | 3.6 (141.5) | 4.4 (172.5) | 4.8 (186.2) |
| PMZ | 2.0 (12.8) | 5.4 (35.3) | 5.0 (32.3) | 6.9 (45.0) | 8.5 (55.2) | 9.3 (60.2) | 9.8 (63.8) |
| TMX | 1.2 (10.0) | 3.1 (25.0) | 5.5 (43.6) | 13.2 (105.8) | 23.4 (187.6) | 31.7 (253.8) | 45.0 (359.9) |
| TFD | 2.5 (16.0) | 6.6 (43.2) | 8.3 (54.0) | 11.7 (76.2) | 15.3 (99.3) | 14.6 (94.8) | 14.0 (91.2) |

The true solubility enhancement by the drug-polymer interaction was calculated by comparing the aqueous solubility with the solubility in presence of the excipient at the same pH. Since the dissolution process of acidic or basic compounds influences the pH of unbuffered water, it was not possible to measure both solubilities at the same pH. Therefore, aqueous solubility values were extrapolated for constant pH 6.0 according to the Henderson-Hasselbalch equation to calculate true solubility enhancement factors (Table 5). Also the non-adjusted values are practically relevant but obtained solubility enhancement is then a confounded effect of molecular excipient interactions as well as pH shift. Another solubility factor could have been a changed solid state during drug dissolution. However, the residual solid analysis confirmed that none of the tested compounds exhibited a solvent-mediated phase transformation. Thus, initial polymorphic forms remained the same during the course of the experiments.

Figure 6:
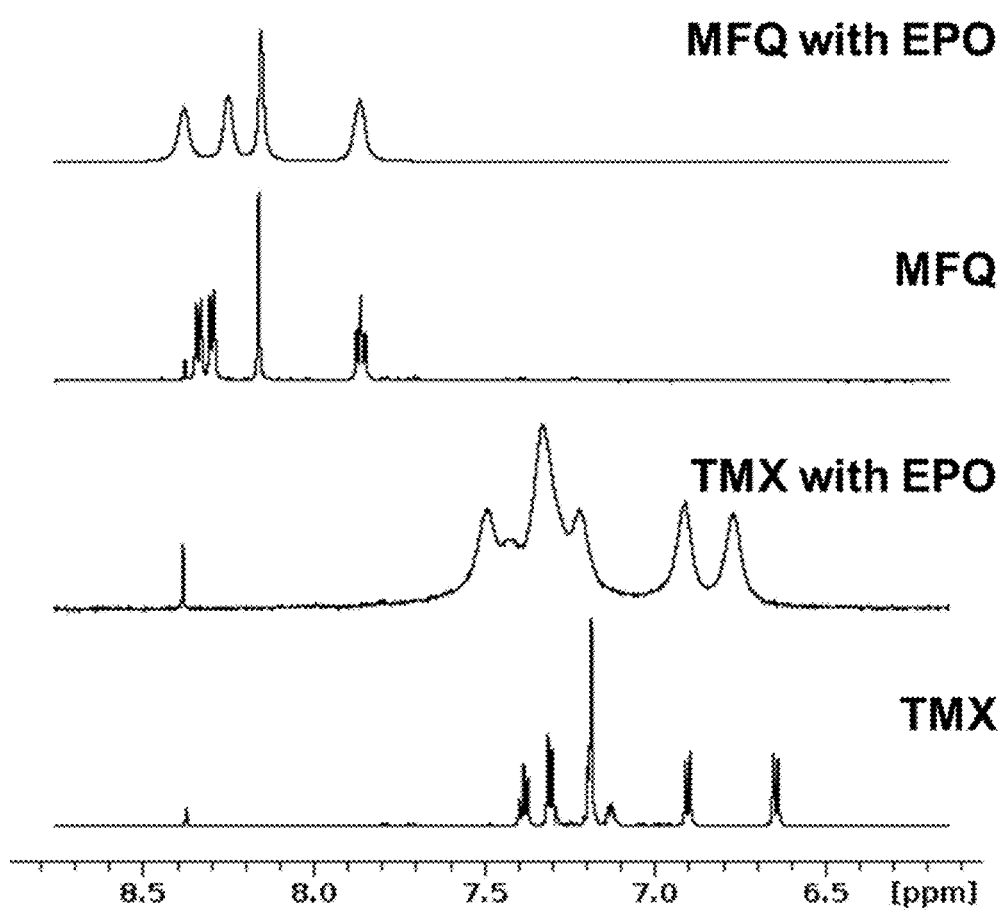
FIG. 6: Solution-state $^1$H NMR spectra of MFQ and TMX in the presence of EPO and in $D_2O$ alone.

$^1$H-NMR Spectroscopy $^1$H-NMR spectra were analyzed to evaluate the interactions between EPO and the different compounds in solution. Peaks originating from protons of aromatic ring systems (present in all API molecules investigated) were observed between 5.50 and 8.50 ppm in $D_2O$ for all APIs. The NMR signals of all APIs in $D_2O$ were very sharp (see FIG. 6), indicating that API-molecules were dispersed in $D_2O$ without substantial aggregation. All drugs had in common that API-related signals displayed changes in line-width in presence of EPO as shown for two examples in FIG. 6. Peaks derived from compounds could be still clearly observed although the peaks' shapes were comparatively much broader.

DOSY $^1$H-NMR was used to determine the diffusion coefficients of the APIs in $D_2O$ with and without 0.5% EPO. Results are displayed in Table 6. The diffusion coefficient of EPO in presence of the APIs was also measured.

TABLE 6

Diffusion coefficient of APIs in $D_2O$ with and without EPO.

| Compound | Diffusion coefficient in $D_2O \cdot 10^{10}$ [m$^2$/s] $D_{API(D2O)}$ | Diffusion coefficient in EPO 0.5% $\cdot 10^{10}$ [m$^2$/s] $D_{API(EPO)}$ | Diffusion coefficient of EPO with API 0.5% $\cdot 10^{10}$ [m$^2$/s] $D_{EPO(API)}$ |
|---|---|---|---|
| CVD | 4.60 | 3.53 | 0.43 |
| CNZ | 4.46 | 3.04 | 0.41 |
| MFQ | 4.65 | 2.62 | 1.03 |
| PMZ | 4.02 | 2.91 | 0.40 |
| TMX | 4.43 | 0.58 | 0.44 |
| TFD | 3.56 | 2.28 | 0.53 |
| EPO* | 0.38 | | |

*Reference value of pure EPO in aqueous solution

As expected, the much larger polymer EPO showed a lower diffusion coefficient in pure $D_2O$ (10 to 15-fold) than the APIs alone. The diffusion coefficient of the APIs decreased slightly in the presence of EPO. Interestingly, the diffusion coefficient of EPO increased in the presence of APIs.

Example 2

Sample Preparation

Polymer solutions were prepared by dissolving EPO (0.1%, 0.5%, 1%, 2%, 3%, 4%, 5% (w/w)) in deionized water and adjusting all solutions to pH 6.0 by hydrochloric acid and sodium hydroxide at 25° C. Solutions were checked carefully for absence of particles.

Solubility and Residual Solid Analysis

Solubility of compounds in EPO-solutions was determined by using a 96-well assay that was introduced to measure equilibrium solubility in parallel to a solid state analysis of the residual solid (SORESOS)[21] as described before.[22] In brief, APIs were dispensed using the powder-picking-method[23] in a 96-well flat bottom plate (Corning Inc., Durham, USA). After addition of stir bars and polymer solutions (150 μl), mixtures were agitated by head-over-head rotation for 48 h at room temperature. After mixing, the suspensions were carefully transferred into 96-well filter plates and the liquid and solid phase were separated by centrifugation. Filtrates were collected, diluted with N-methyl-2-pyrrolidone and drug content in filtrates was determined using a Waters Acquity Ultra Performance Liquid Chromatographic (UPLC) system equipped with a 2996 Photodiode Array Detector and an Acquity UPLC BEH C18 column (2.1×50 mm, 1.7 μm particle size) from Waters (Milford, USA). An isocratic flow (composition of the mobile phase is listed in Table 7) was applied for 0.3 min at a flow rate of 0.75 mL/min. Subsequently, the concentration of solvent B was linearly increased to 100% within 0.5 min. Solid state analysis of residual solid was performed by X-ray powder diffraction (XRPD) using a STOE Stadi P Combi diffractometer with a primary Ge-monochromator (Cu Kα radiation), imaging plate position sensitive detector (IP-PSD), and a 96-well sample stage as described before.[21] The IP-PSD allowed simultaneous recording of the diffraction pattern on both sides of the primary beam which were summed up by the software STOE WinXPOW to reduce effects related to poor crystal orientation statistics. Samples were analyzed directly in the 96-well filter plate with an exposure time of 5 min per well.

TABLE 7

UPLC analytic.

| Compound | Mobile phase A:B [%] | Detection wavelength [nm] |
|---|---|---|
| Danazol (DNZ) | 40:60 | 285 |
| Felodipine (FLP) | 40:60 | 283/360 |
| Fenofibrate (FNF) | 30:70 | 286 |
| Griseofulvin (GFN) | 70:30 | 293 |
| Nifedipine (NFP) | 70:30 | 235 |

$^a$Mobile phase A: deionized water with 0.1% (v/v) triethylamine adjusted to pH 2.2 with methanesulfonic acid
Mobile phase B: acetonitrile.

Results

Figure 8:
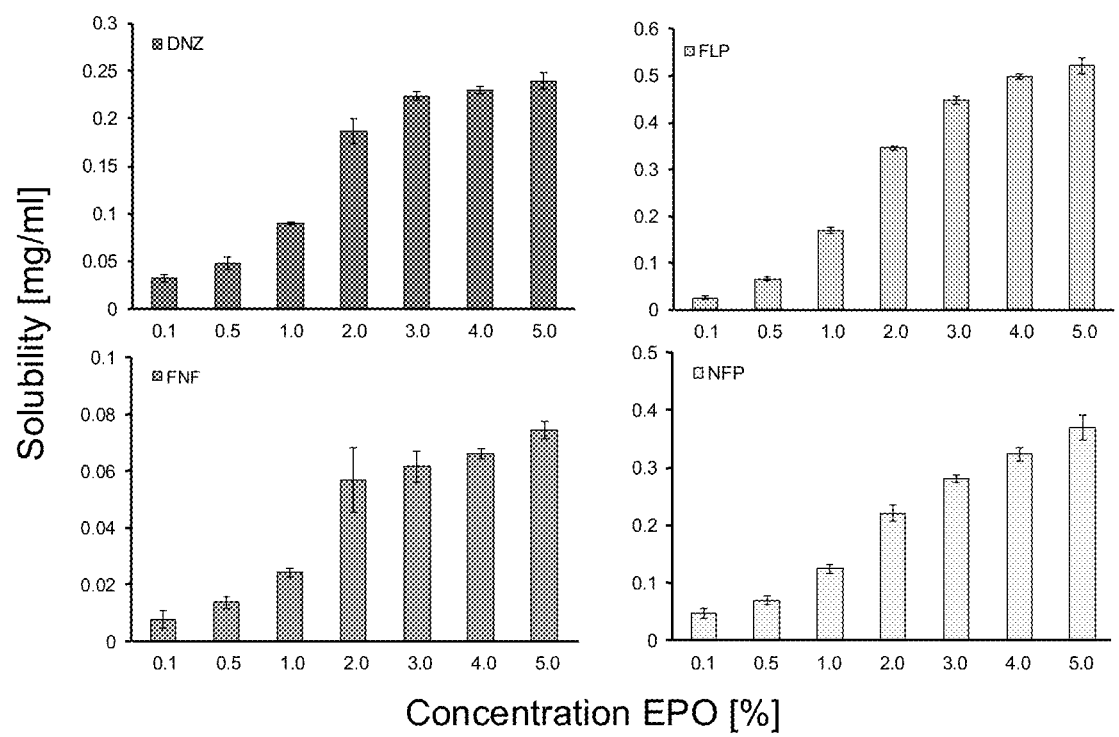
FIG. 8: Solubility of DNZ, FLP, FNF, and NFP in EPO-solutions after 48 h at room temperature.
Figure 9:
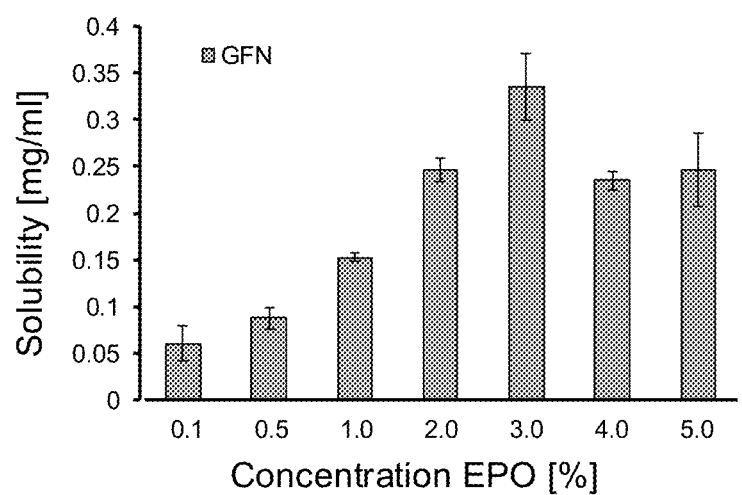
FIG. 9. Solubility of GFN in EPO-solutions after 48 h at room temperature.

All excipient solutions were adjusted to pH 6.0 before incubation and following equilibration, the residual solid was analyzed by means of XRPD. Compared to water, all model compounds displayed a good solubility enhancement (SE) in the different EPO-solutions (FIGS. 8-9 and Table 8). DNZ and FNF (FIG. 8) solubility reached a plateau at 3% and 2% EPO (w/w), respectively. In contrast, FLP and NFP (FIG. 8) showed an increase of solubility with polymer concentration up to 5% EPO. GFN (FIG. 9) reached a maximum solubility at 2% EPO (w/w) and its solubility increased with the polymer concentration. Above 2% EPO, solubility decreased again and finally reached a kind of plateau. The residual solid analysis confirmed that none of the tested compounds changed its polymorphic form. Therefore, it is likely that the SE (Table 8) resulted from drug-EPO interactions in the bulk phase and not from stabilization of a metastable polymorphic form.

TABLE 8

Solubility enhancement (SE) factors of model compounds in EPO-solutions (0.1-5%) compared to solubility in water. SE factors were calculated by dividing the solubility of a compound in polymer solutions by the solubility in water.

| Compound | SE in EPO | | | | | | |
|---|---|---|---|---|---|---|---|
| | 0.1% | 0.5% | 1.0% | 2.0% | 3.0% | 4.0% | 5.0 |
| DNZ | 32 | 90 | 89 | 187 | 224 | 230 | 240 |
| FLP | 26 | 66 | 170 | 346 | 447 | 498 | 522 |
| FNF | 8 | 14 | 24 | 57 | 62 | 66 | 75 |
| GFN | 60 | 87 | 152 | 247 | 336 | 235 | 247 |
| NFP | 1 | 2 | 2 | 4 | 5 | 5 | 6 |

CITED REFERENCES

1. Lipinski, C. A.; Lombardo, F.; Dominy, B. W.; Feeney, P. J. Experimental and computational approaches to estimate solubility and permeability in drug discovery and development settings. *Adv. Drug Deliv. Rev.* 1997, 23, (1-3), 3-25.
2. Bergström, C. A.; Norinder, U.; Luthman, K.; Artursson, P. Experimental and computational screening models for prediction of aqueous drug solubility. *Pharm. Res.* 2002, 19, (2), 182-188.
3. Humberstone, A. J.; Charman, W. N. Lipid-based vehicles for the oral delivery of poorly water soluble drugs. *Adv. Drug Deliv. Rev.* 1997, 25, (1), 103-128.
4. Van den Mooter, G. The use of amorphous solid dispersions: A formulation strategy to overcome poor solubility and dissolution rate. *Drug Discovery Today: Technologies* 2012, 9, (2), e79-326 e85.
5. Kuentz, M. Lipid-based formulations for oral delivery of lipophilic drugs. *Drug Discovery Today: Technologies* 2012, 9, (2), e97-e104.
6. Desai, P. P.; Date, A. A.; Patravale, V. B. Overcoming poor oral bioavailability using nanoparticle formulations—opportunities and limitations. *Drug Discovery Today: Technologies* 2012, 9, (2), e87-e95.
Li, P.; Zhao, L. Developing early formulations: Practice and perspective. *Int. J. Pharm.* 2007, 341, (1-2), 1-19.
8. Lee, Y.-C.; Zocharski, P. D.; Samas, B. An intravenous formulation decision tree for discovery compound formulation development. *Int. J. Pharm.* 2003, 253, (1-2), 111-119.
9. Song, Y.; Yang, X.; Chen, X.; Nie, H.; Byrn, S.; Lubach, J. W. Investigation of Drug—Excipient Interactions in Lapatinib Amorphous Solid Dispersions Using Solid-State NMR Spectroscopy. *Molecular Pharmaceutics* 2015, 12, (3), 857-866.
10. Serajuddin, A. T. M. Solid dispersion of poorly water-soluble drugs: Early promises, subsequent problems, and recent breakthroughs. *J. Pharm. Sci.* 1999, 88, (10), 1058-1066.
11. Taylor, L. S.; Zografi, G. Spectroscopic Characterization of Interactions Between PVP and Indomethacin in Amorphous Molecular Dispersions. *Pharm. Res.* 1997, 14, (12), 1691-1698.
12. Gallardo, D.; Skalsky, B.; Kleinebudde, P. Controlled release solid dosage forms using combinations of (meth) acrylate copolymers. *Pharm. Dev. Technol.* 2008, 13, (5), 413-423.
13. Higashi, K.; Yamamoto, K.; Pandey, M. K.; Mroue, K. H.; Moribe, K.; Yamamoto, K.; Ramamoorthy, A. Insights into Atomic-Level Interaction between Mefenamic Acid and Eudragit EPO in a Supersaturated Solution by High-Resolution Magic-Angle Spinning NMR Spectroscopy. *Molecular Pharmaceutics* 2014, 11, (1), 351-357.
14. Kojima, T.; Higashi, K.; Suzuki, T.; Tomono, K.; Moribe, K.; Yamamoto, K. Stabilization of a Supersaturated Solution of Mefenamic Acid from a Solid Dispersion with EUDRAGIT(A®) EPO. 351 *Pharm. Res.* 2012, 29, (10), 2777-2791.
15. Li, J.; Lee, I. W.; Shin, G. H.; Chen, X.; Park, H. J. Curcumin-Eudragit® EPO solid dispersion: A simple and potent method to solve the problems of curcumin. *Eur. J Pharm. Biopharm.* 2015, 94, 322-354
16. Doreth, M.; Löbmann, K.; Grohganz, H.; Holm, R.; Lopez de Diego, H.; Rades, T.; Priemel, P. A. Glass solution formation in water—In situ amorphization of naproxen and ibuprofen with Eudragit® EPO. *Journal of Drug Delivery Science and Technology.*
17. Priemel, P. A.; Laitinen, R.; Grohganz, H.; Rades, T.; Strachan, C. J. In situ amorphisation of indomethacin with Eudragit® E during dissolution. *Eur. J Pharm. Biopharm.* 2013, 85, (3, Part B), 1259-1265.
18. Saal, W.; Ross, A.; Wyttenbach, N.; Alsenz, J.; Kuentz, M. A Systematic Study of Molecular Interactions of Anionic Drugs with a Dimethylaminoethyl Methacrylate Copolymer Regarding Solubility Enhancement. *Molecular Pharmaceutics* 2017, 14, (4), 1243-1250.
19. Higashi, K.; Seo, A.; Egami, K.; Otsuka, N.; Limwikrant, W.; Yamamoto, K.; Moribe, K. Mechanistic insight into the dramatic improvement of probucol dissolution in neutral solutions by solid dispersion in Eudragit EPO with saccharin. *J. Pharm. Pharmacol.* 2015.
20. Kanaya, H.; Ueda, K.; Higashi, K.; Yamamoto, K.; Moribe, K. Stabilization mechanism of nitrazepam supersaturated state in nitrazepam/Eudragit® EPO/saccharin solution revealed by NMR measurements. *asian journal of pharmaceutical sciences* 2016, 11, (1), 58-59.
21. Wyttenbach, N.; Alsenz, J.; Grassmann, O. Miniaturized assay for solubility and residual solid screening (SORE-SOS) in early drug development. *Pharm. Res.* 2007, 24, (5), 888-898.
22. Kirchmeyer, W.; Wyttenbach, N.; Alsenz, J.; Kuentz, M. Influence of Excipients on Solvent-Mediated Hydrate Formation of Piroxicam Studied by Dynamic Imaging and Fractal Analysis. *Cryst. Growth Des.* 2015, 15, (10), 5002-5010.
23. Alsenz, J. Powder Picking: An inexpensive, manual, medium-throughput method for powder dispensing. *Powder Technol.* 2011, 209, (1-3), 152-157.
24. Wu, D. H.; Chen, A. D.; Johnson, C. S. An Improved Diffusion-Ordered Spectroscopy Experiment Incorporating Bipolar-Gradient Pulses. *Journal of Magnetic Resonance, Series A* 1995, 115, (2), 260-264.
25. Völgyi, G.; Baka, E.; Box, K. J.; Comer, J. E. A.; Takács-Novák, K. Study of pH-dependent solubility of organic bases. Revisit of Henderson-Hasselbalch relationship. *Analytica Chimica Acta* 2010, 673, (1), 40-46.
26. Dobrynin, A. V.; Rubinstein, M. Theory of polyelectrolytes in solutions and at surfaces. *Progress in Polymer Science* 2005, 30, (11), 1049-1118.
27. Solis, F. J.; de la Cruz, M. O. Collapse of flexible polyelectrolytes in multivalent salt solutions. *The Journal of Chemical Physics* 2000, 112, (4), 2030-2035. 387
28. Yalkowsky, S. H.; He, Y.; Jain, P., *Handbook of aqueous solubility data.* CRC press: 2016.

The invention claimed is:

1. A pharmaceutical preparation, consisting of:
water;
a lipophilic, basic or neutral, low molecular weight active pharmaceutical ingredient; and
EPO, wherein EPO is a methacrylic acid copolymer composed of dimethylaminoethyl methacrylate, butyl methacrylate, and methyl methacrylate with a molar ratio of 2:1:1,
wherein the pharmaceutical preparation is a liquid aqueous solution.

2. The pharmaceutical preparation according to claim 1, wherein the low molecular weight active pharmaceutical ingredient is present in an amount from 0.000001% (w/w) to 20% (w/w), and the EPO is present in an amount from 0.01% (w/w) to 20% (w/w).

3. The pharmaceutical preparation according to claim 1, wherein the low molecular weight active pharmaceutical ingredient is present in an amount from 0.00001% (w/w) to 10% (w/w), and the EPO is present at 0.1%, 0.5%, 1%, 2%, 3%, 4%, or 5% (w/w).

4. The pharmaceutical preparation according to claim 1, wherein the lipophilic low molecular weight active pharmaceutical ingredient is basic and positively charged.

5. The pharmaceutical preparation according to claim 2, wherein the lipophilic low molecular weight active pharmaceutical ingredient is basic and positively charged.

6. The pharmaceutical preparation according to claim 1, wherein the lipophilic low molecular weight active pharmaceutical ingredient is neutral and without charge.

7. The pharmaceutical preparation according to claim 2, wherein the lipophilic low molecular weight active pharmaceutical ingredient is neutral and without charge.

8. A method of treating a patient, comprising administering to the patient a pharmaceutical preparation according to claim 1.

9. The method of claim 8, wherein the pharmaceutical preparation is administered orally or topically.

10. A kit, comprising the pharmaceutical preparation according to claim 1, and instructions for how to prepare and administer the pharmaceutical preparation to a patient in need thereof.

* * * * *